United States Patent
Mitra et al.

(10) Patent No.: US 11,679,771 B2
(45) Date of Patent: Jun. 20, 2023

(54) VEHICLE EVENT IDENTIFICATION

(71) Applicant: Ford Global Technologies, LLC, Dearborn, MI (US)

(72) Inventors: Pramita Mitra, Bloomfield Hills, MI (US); Yifan Chen, Ann Arbor, MI (US); Jayanthi Rao, West Bloomfield, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 333 days.

(21) Appl. No.: 16/490,647

(22) PCT Filed: Mar. 3, 2017

(86) PCT No.: PCT/US2017/020655
§ 371 (c)(1),
(2) Date: Sep. 3, 2019

(87) PCT Pub. No.: WO2018/160192
PCT Pub. Date: Sep. 7, 2018

(65) Prior Publication Data
US 2020/0001881 A1    Jan. 2, 2020

(51) Int. Cl.
*B60W 40/08* (2012.01)
*A61B 5/024* (2006.01)
*A61B 5/0533* (2021.01)
*G06F 1/16* (2006.01)

(52) U.S. Cl.
CPC ............. *B60W 40/08* (2013.01); *A61B 5/024* (2013.01); *A61B 5/0533* (2013.01); *G06F 1/163* (2013.01); *B60W 2040/0872* (2013.01)

(58) Field of Classification Search
CPC .......... B60W 40/08; B60W 2040/0872; A61B 5/024; A61B 5/0533; A61B 5/18; G06F 1/163
See application file for complete search history.

(56) References Cited

U.S. PATENT DOCUMENTS

| 8,340,438 B2 | 12/2012 | Anderson |
| 9,201,421 B1 | 12/2015 | Fairfield et al. |
| 9,333,954 B2 | 5/2016 | Schneider |
| 9,500,495 B2 | 11/2016 | Nomura |

(Continued)

FOREIGN PATENT DOCUMENTS

| CN | 105631977 A | 6/2016 | |
| KR | 1020150077360 | * 7/2015 | ............ B60W 50/08 |
| WO | 2015030920 A1 | 3/2015 | |

OTHER PUBLICATIONS

Notification of International Preliminary Report on Patentability dated Sep. 12, 2019 with Transmittal of International Search Report and Written Opinion of International Searching Authority regarding International Application No. PCT/US2017/020655 (18 pages).

(Continued)

*Primary Examiner* — Elaine Gort
*Assistant Examiner* — Chanmin Park
(74) *Attorney, Agent, or Firm* — Brandon Hicks; Bejin Bieneman PLC (57) ABSTRACT

Biometric data are collected about a user in a vehicle. A user is prompted to provide an input on a wearable device to identify an object based on the biometric data.

20 Claims, 5 Drawing Sheets

(56) References Cited

U.S. PATENT DOCUMENTS

| | | | |
|---|---|---|---|
| 9,878,663 B1* | 1/2018 | Kochura | B60W 50/0098 |
| 2012/0287123 A1 | 11/2012 | Starner | |
| 2013/0132434 A1 | 5/2013 | Scofield et al. | |
| 2014/0022108 A1 | 1/2014 | Alberth, Jr. et al. | |
| 2014/0249722 A1 | 9/2014 | Hegemann et al. | |
| 2014/0364752 A1 | 12/2014 | Dugan et al. | |
| 2015/0084757 A1* | 3/2015 | Annibale | G08B 25/016 |
| | | | 340/436 |
| 2015/0254986 A1 | 9/2015 | Fairfield et al. | |
| 2016/0001781 A1* | 1/2016 | Fung | B60K 28/02 |
| | | | 701/36 |
| 2016/0163198 A1* | 6/2016 | Dougherty | G08G 1/162 |
| | | | 340/905 |
| 2022/0005291 A1* | 1/2022 | Konrardy | G07C 5/008 |

OTHER PUBLICATIONS

Chinese Office Action as issued by the Chinese Patent Office dated Nov. 30, 2021 (in Chinese and English).

* cited by examiner

VEHICLE EVENT IDENTIFICATION

BACKGROUND

Vehicles traveling on roadways may encounter obstacles that can impede operation of the vehicle. For example, animals crossing a roadway may require a user to apply a brake to stop the vehicle. An autonomous vehicle that encounters the obstacle can detect the obstacle and can actuate components to change vehicle operation to address the obstacle. Furthermore, an operator of a non-autonomous or partially autonomous vehicle can identify the obstacle and actuate components to address the obstacle. A first vehicle may detect and or identify obstacles, and information concerning the obstacle could be of use to a second vehicle. However, systems are lacking to allow vehicles to share and/or utilize obstacle information.

DETAILED DESCRIPTION

A system comprises a computer programmed to collect biometric data about a user in a vehicle. Based on the biometric data, the computer is programmed to prompt a user to provide an input on a wearable device to identify an object. The computer can be further programmed to actuate a vehicle sensor upon receiving the input. The computer can be further programmed to prompt the user upon receiving a request from another vehicle to identify the object. The computer can be further programmed to stop prompting a predetermined period of time after a biometric data threshold had been met and user input has not been received.

The biometric data can include at least one of a galvanic skin response and a heart rate of the user. The computer can be further programmed to prompt the user when the galvanic skin response exceeds a galvanic skin response threshold. The computer can be further programmed to prompt the user when the heart rate exceeds a heart rate threshold.

The computer can be further programmed to send a message to another vehicle with the input from the user identifying the object. The computer can be further programmed to present captured visual data of the object on a display of the wearable device. The computer can be further programmed to collect data with a vehicle sensor and, based on the data from the vehicle sensor and the biometric data, prompt the user to provide an input on a wearable device to identify the object.

A method comprises collecting biometric data about a user in a vehicle and, based on the biometric data, prompting a user to provide an input on a wearable device to identify an object. The method can further comprise actuating a vehicle sensor upon receiving the input. The method can further comprise prompting the user upon receiving a request from another vehicle to identify the object. The method can further comprise stopping to prompt the user after a predetermined period of time after a biometric data threshold had been met and user input has not been received.

In the method, the biometric data can include at least one of a galvanic skin response and a heart rate of the user. The method can further comprise prompting the user when the galvanic skin response exceeds a galvanic skin response threshold. The method can further comprise prompting the user when the heart rate exceeds a heart rate threshold.

The method can further comprise sending a message to another vehicle with the input from the user identifying the event. The method can further comprise presenting captured visual data of the event on a display of the wearable device. The method can further comprise collecting data with a vehicle sensor and, based on the data from the vehicle sensor and the biometric data, prompting the user to provide an input on a wearable device to identify the object.

Further disclosed is a computing device programmed to execute any of the above method steps. Yet further disclosed is a vehicle comprising the computing device. Yet further disclosed is a computer program product, comprising a computer readable medium storing instructions executable by a computer processor, to execute any of the above method steps.

A computer can be programmed to collect biometric data about a user in a vehicle and, based on the biometric data, to prompt the user to provide an input to a wearable device to identify an event outside of the vehicle. Based on the input after and in response to the prompt, the computer is further programmed to identify the event. By incorporating the user input, the computer can identify events that the computer typically would be unable to identify within an acceptable degree of confidence. Furthermore, the user input can identify events that occur in areas where events are less frequently identified, e.g., rural areas. Thus, rather than relying on a certain number of vehicles to identify events, the event can be identified with higher confidence with the user input.

As used herein, an "event" is a detection of one or more identified objects on or near a roadway. That is, the objects can cause a disruption of typical operation of the vehicle on the roadway, and by identifying the objects and broadcasting the event identified from the objects to one or more other vehicles, the other vehicles can avoid the objects. Example events include, e.g., detection of an obstacle such as a pothole or downed tree, a crash scene, a lane closure, an animal crossing, potholes, construction, etc.

Figure 1:
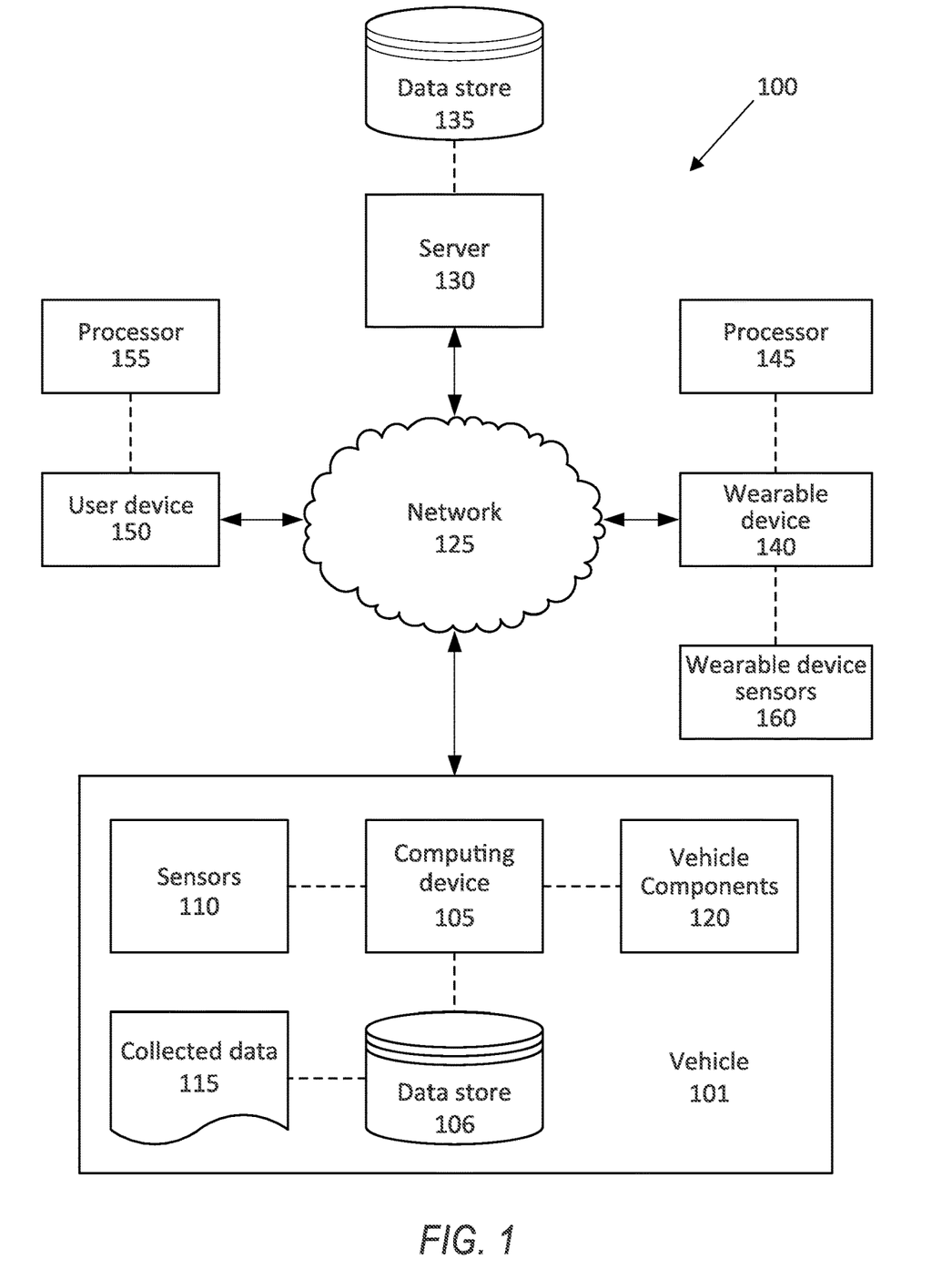
FIG. 1 is a block diagram of an example system for identifying an event.

FIG. 1 illustrates a system 100 for identifying an event near a vehicle 101. A computing device 105 in the vehicle 101 is programmed to receive collected data 115 from one or more sensors 110. For example, vehicle 101 data 115 may include a location of the vehicle 101, a location of a target, etc. Location data may be in a known form, e.g., geo-coordinates such as latitude and longitude coordinates obtained via a navigation system, as is known, that uses the Global Positioning System (GPS). Further examples of data 115 can include measurements of vehicle 101 systems and components, e.g., a vehicle 101 velocity, a vehicle 101 trajectory, etc.

The computing device 105 is generally programmed for communications on a vehicle 101 network, e.g., including a communications bus, as is known. Via the network, bus, and/or other wired or wireless mechanisms (e.g., a wired or wireless local area network in the vehicle 101), the computing device 105 may transmit messages to various devices in a vehicle 101 and/or receive messages from the various devices, e.g., controllers, actuators, sensors, etc., including sensors 110. Alternatively or additionally, in cases where the computing device 105 actually comprises multiple devices, the vehicle network may be used for communications between devices represented as the computing device 105 in this disclosure. In addition, the computing device 105 may be programmed for communicating with the network 125, which, as described below, may include various wired and/or wireless networking technologies, e.g., cellular, Bluetooth®, Bluetooth® Low Energy (BLE), wired and/or wireless packet networks, etc.

The data store 106 may be of any known type, e.g., hard disk drives, solid state drives, servers, or any volatile or non-volatile media. The data store 106 may store the collected data 115 sent from the sensors 110.

Sensors 110 may include a variety of devices. For example, as is known, various controllers in a vehicle 101 may operate as sensors 110 to provide data 115 via the vehicle 101 network or bus, e.g., data 115 relating to vehicle speed, acceleration, position, subsystem and/or component status, etc. Further, other sensors 110 could include cameras, motion detectors, etc., i.e., sensors 110 to provide data 115 for evaluating a location of a target, projecting a path of a target, evaluating a location of a roadway lane, etc. The sensors 110 could also include short range radar, long range radar, LIDAR, and/or ultrasonic transducers.

Collected data 115 may include a variety of data collected in a vehicle 101. Examples of collected data 115 are provided above, and moreover, data 115 are generally collected using one or more sensors 110, and may additionally include data calculated therefrom in the computing device 105, and/or at the server 130. In general, collected data 115 may include any data that may be gathered by the sensors 110 and/or computed from such data.

The vehicle 101 may include a plurality of vehicle components 120. As used herein, each vehicle component 120 includes one or more hardware components adapted to perform a mechanical function or operation—such as moving the vehicle, slowing or stopping the vehicle, steering the vehicle, etc. Non-limiting examples of components 120 include a propulsion component (that includes, e.g., an internal combustion engine and/or an electric motor, etc.), a transmission component, a steering component (e.g., that may include one or more of a steering wheel, a steering rack, etc.), a brake component, a park assist component, an adaptive cruise control component, an adaptive steering component, and the like.

The system 100 may further include a network 125 connected to a server 130 and a data store 135. The computer 105 may further be programmed to communicate with one or more remote sites such as the server 130, via the network 125, such remote site possibly including a data store 135. The network 125 represents one or more mechanisms by which a vehicle computer 105 may communicate with a remote server 130. Accordingly, the network 125 may be one or more of various wired or wireless communication mechanisms, including any desired combination of wired (e.g., cable and fiber) and/or wireless (e.g., cellular, wireless, satellite, microwave, and radio frequency) communication mechanisms and any desired network topology (or topologies when multiple communication mechanisms are utilized). Exemplary communication networks include wireless communication networks (e.g., using Bluetooth®, BLE, IEEE 802.11, vehicle-to-vehicle (V2V) such as Dedicated Short Range Communications (DSRC), etc.), local area networks (LAN) and/or wide area networks (WAN), including the Internet, providing data communication services.

The system 100 may include a wearable device 140. As used herein, a "wearable device" is a portable computing device including a structure so as to be wearable on a person's body (e.g., as a watch or bracelet, as a pendant, etc.), and that includes a memory, a processor, a display, and one or more input mechanisms, such as a touchscreen, buttons, etc., as well as hardware and software for wireless communications such as described herein. A wearable device 140 will be of a size and shape to be fitted to or worn on a person's body, e.g., a watch-like structure including bracelet straps, etc., and as such typically will have a smaller display than a user device 150, e.g., ⅓ or ¼ of the area. For example, the wearable device 140 may be a watch, a smart watch, a vibrating apparatus, etc. that includes capabilities for wireless communications using IEEE 802.11, Bluetooth®, and/or cellular communications protocols. Further, the wearable device 140 may use such communications capabilities to communicate via the network 125 and also directly with a vehicle computer 105, e.g., using Bluetooth®. The wearable device 140 includes a wearable device processor 145.

The system 100 may include a user device 150. As used herein, a "user device" is a portable, non-wearable computing device that includes a memory, a processor, a display, and one or more input mechanisms, such as a touchscreen, buttons, etc., as well as hardware and software for wireless communications such as described herein. That the user device 150 is "non-wearable" means that it is not provided with any structure to be worn on a person's body; for example, a smart phone user device 150 is not of a size or shape to be fitted to a person's body and typically must be carried in a pocket or handbag, and could be worn on a person's body only if it were fitted with a special case, e.g., having an attachment to loop through a person's belt, and hence the smart phone user device 150 is non-wearable. Accordingly, the user device 150 may be any one of a variety of computing devices including a processor and a memory, e.g., a smartphone, a tablet, a personal digital assistant, etc. the user device 150 may use the network 125 to communicate with the vehicle computer 105 and the wearable device 140. For example, the user device 150 and wearable device 140 can be communicatively coupled to each other and/or to the vehicle computer 105 with wireless technologies such as described above. The user device 150 includes a user device processor 155.

The wearable device processor 145 and the user device processor 155 can instruct the computing device 105 to actuate one or more components 120. A user can provide an input to an icon on a wearable device 140 display, e.g., by touching the icon. Based on the user input, the wearable device processor 145 can message the user device processor 155 and/or the computing device 105 to actuate the components 120 associated with the input.

The wearable device 140 can include one or more wearable device sensors 160. The wearable device sensors 160 can collect data 115 from the user. The wearable device sensors 160 can be a variety of devices, e.g., a heart rate sensor, a galvanic skin response sensor, a camera, a microphone, an accelerometer, a gyroscope, etc. The wearable device processor 145 can instruct the wearable device sensors 160 to collect data 115 and, based on the data 115, prompt the user to provide input about the event.

Figure 2:
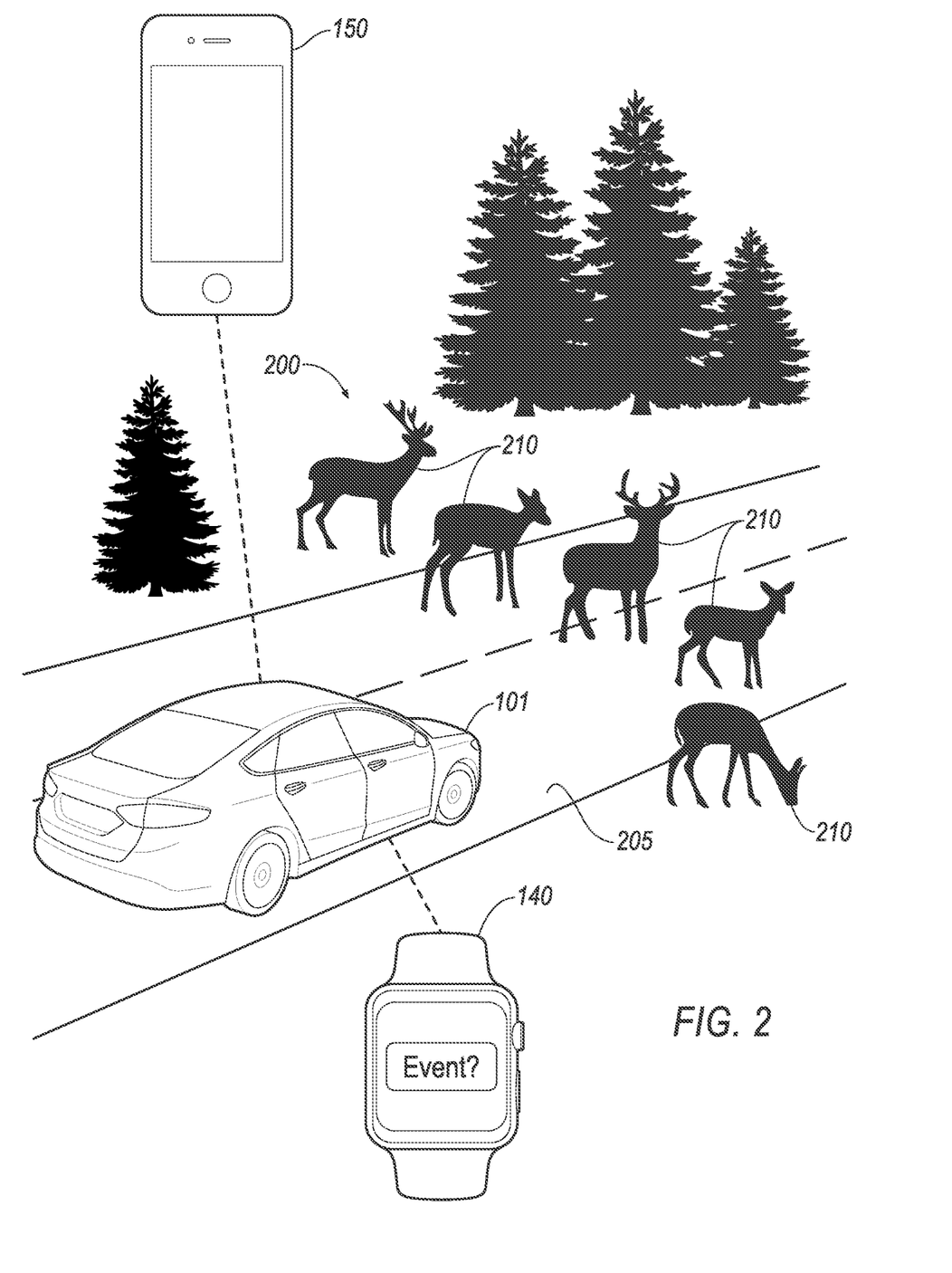
FIG. 2 illustrates an example event and a prompt for user input.

FIG. 2 illustrates an example event 200 identified by the user in the vehicle 101. The vehicle 101 travels on a roadway 205. While on the roadway 205, the sensors 110 can collect data 115 about objects 210 around the vehicle 101. The computing device 105 can use the data 115 about the objects 210 to identify the event 200 on the roadway 205. That is, the computing device 105 can store information specifying data values indicating each of a plurality of events 200 in the data store 106 and/or the server 130, and the computing device 105 can compare the stored information about the objects 210 to collected data 115 to determine whether one of these stored events 200 is the event 200 on the roadway 205. For example, the computing device 105 can receive image data 115 about objects 210 moving in front of the vehicle 101 on the roadway 205 and audio data 115 from the wearable device 140 that, when parsed with a known text-parsing technique, includes the word "deer." Based on the image data 115 and the audio data 115, the computing device 105 can determine that the objects are deer and the event 200 is an animal crossing.

In certain situations, the data 115 collected by the computing device 105 may not correspond to one of the stored events 200. That is, each stored event 200 can include one or more objects 210 detected to generate the event 200. Upon detecting the objects 210 associated with the event 200, the computing device 105 can generate and store the event 200. The stored events 200 can be based on identification of objects from a plurality of other vehicles 101 and stored on the server 130. Thus, in a densely populated area with a plurality of vehicles 101 to identify objects 210, the server 130 can store more events 200 and the computing device 105 can more easily identify the event 200 based on the detected objects 210. Whether a particular event 200 is stored in the server 130 can be based on whether one or more vehicles 101 have identified objects 210 associated with the event 200. For example, if the event 200 is in a less-populated area, fewer vehicles 101 may have collected data 115 about the event 200 than if in a more densely populated area.

When the computing device 105 cannot identify the event 200, the computing device 105 can prompt a user in the vehicle 101 to provide an input to identify the event 200. The input can be, e.g., an audio input recorded by a microphone in the wearable device 140, a text input, etc. The wearable device processor 145 can send the input to the computing device 105. In the example of FIG. 2, the event 200 can be deer crossing the roadway 205. The computing device 105 may not have an event 200 stored of deer crossing the roadway 205, and the computing device 105 can thus fail to identify the event 200. Alternatively or additionally, the computing device 105 can communicate with the user device processor 155 to prompt the user on the user device 150 display for input about the event 200.

Upon receiving an input from the user, the computing device 105 can identify the event 200. Based on the input, the computing device 105 can actuate one or more sensors 110 to collect data 115 based on the input. For example, the computing device 105 can use a text-parsing technique, as is known, to convert the user's audio input into words that the computing device 105 can analyze, including text such as "deer." Based on the parsed text, the computing device 105 can, using known techniques, actuate one or more sensors 110 to collect data 115. For example, if the text parsed includes "deer," the computing device 105 can actuate a camera 110 to collect image data 115 of the objects 210 ahead of the vehicle 101 and determine whether there are deer in front of the vehicle 101.

The computing device 105 can determine to stop prompting the user to provide input about the event 200. When the computing device 105 determines that the user is not going to provide input and/or the objects 210 have passed, the computing device can send a message to the wearable device processor 145 to stop prompting the user on the wearable device 140 display. For example, the computing device 105 can determine to stop prompting the user after a predetermined period of time. In another example, the computing device 105 can determine to stop prompting the user upon receiving data 115 indicating that the event 200 has ended, e.g., there are no more animals crossing the roadway.

The computing device 105 can determine an identification confidence value for the identification of the event 200. As used herein, an "identification confidence value" is a numerical value (e.g., between 0 and 1) that indicates the confidence that computing device 105 has correctly identified the event. The computing device 105 may evaluate the quality of the data 115, e.g., image quality, clarity of objects detected, precision of data 115, accuracy of data 115, completeness of data 115, etc., using known techniques, to determine the identification confidence value. The computing device 105 can send a message with the event 200 identified, the identification confidence value, and the location of the vehicle 101. The computing device 105 can be programmed to send the message when the identification confidence value is above a predetermined confidence threshold. The confidence threshold can be determined based on the sensors 110 used to collect the data 115 and the reliability of the sensors 110 used.

Semi-autonomous and autonomous vehicles can have high-resolution three-dimensional (3D) maps for navigating in city environments. The standard method is for 3D object classification in a known space is done by matching the captured 3D objects (from the external camera feed) against known 3D objects for similarity. However, in areas with less frequent travel (e.g., rural areas, national parks, etc.), there could be previously unseen 3D objects. Classification of unknown 3D objects can require representation in a way that captures the global and local properties of the object. This can be achieved by creating a 3D descriptor that summarizes salient shape properties of the object.

3D object classification can be performed by assigning the 3D objects to one of a set of previously defined 3D object classes. Typically, a learning technique can be used to identify salient points on the new 3D objects. The patterns of these salient points are then used to train a classifier for object class identification by transforming the patterns onto a two-dimensional (2D) map using coordinate transformation. Before mapping the salient patterns onto the 2D plane, the salient patterns are assigned a confidence score by the classifier. The possible range of the classifier confidence scores could be discretized into a number of bins. If the confidence score did not fall within a specific subset of bins, human user input could be sought.

A salient feature matrix can be created by applying a low-level operator (e.g., Gaussian absolute curvature or mean curvature) to extract local properties of the surface by computing a single feature value $v_i$ for every point $p_i$ on a surface mesh. The low-level feature value for every point $p_i$ on the surface mesh can be aggregated into a mid-level feature vector for a given neighborhood boundary specification. This could be achieved by creating local histograms of the low-level features which could be used to train a multi-class classifier, e.g., a Support Vector Machine (SVM), to get scores of membership of point $p_i$ to each of the existing class $y_i$. For example, a case of 3 classes could result in 3 scores: Score($y_a|p_i$), Score($y_b|p_i$), Score($y_c|p_i$). Converting these scores into probability memberships $P(y_a|p_i) > P(y_b|p_i) > P(y_c|p_i)$, the most probable class of $p_i$ could be determined as $y_a$.

The wearable device 140 can include sensors 160, as described above, that collect biometric data 115 of the user. The biometric data 115 can include, e.g., skin temperature, galvanic skin response, heart rate, etc. For example, galvanic skin response data 115 can measure the electric conductivity (measured in microSiemens, or μS) of the occupant's skin, i.e., the ability for electricity to conduct across the occupant's skin. A user with sweaty skin (e.g., noticing an upcoming event 200 that heightens the user's awareness) would have a higher conductivity than a user with dry skin. The biometric data 115 can be used to signal the wearable device processor 145 to prompt the user for an input. For example, if the electric conductivity of the user is above a predetermined galvanic response threshold (e.g., a value greater than the conductivity of dry skin and less than the conductivity wet skin), then the wearable device processor 145 can prompt the user to identify the event 200. In another example, when the heart rate sensor 160 determines that the heart rate is above a heart rate threshold, the wearable device processor 145 can prompt the user to identify the event 200.

The computing device 105 can communicate with the server 130 and/or other vehicles 101 to broadcast the event 200. The computing device 105 can determine a location of the vehicle 101 and send a message over the network 125 with the location of the vehicle 101 and the input provided by the user. If the computing device 105 identified the event 200 upon receiving the user input, the computing device 105 can include the identified event 200 in the message.

The computing device 105 can present captured visual data 115 of the objects 210 on the wearable device 140 display. That is, upon collecting data 115 from, e.g., a camera 110, the computing device 105 can present one or more images from the data 115 of the objects 210 on the wearable device 140 display to prompt the user to identify the event 200. By displaying visual data 115 on the wearable device 140 display, the user can provide additional information about the event 200, and the computing device 105 can identify the event 200 with a greater identification confidence value, as described above.

The wearable device 140 can include a haptic device. The haptic device generates a vibration and/or flashes a light that is transmitted to the user. The wearable device processor 145 can actuate the haptic device based on receiving an input from the user and/or messages from the computing device 105. The haptic device can be disposed in a wrist band of the wearable device 140, and/or the haptic device can be located in another location in the wearable device 140, e.g., behind the display. Additionally or alternatively, the user device 150 can include a haptic device that can be instructed to vibrate by, e.g., the user device processor 155, the wearable device processor 145, and/or the computing device 105. That is, the computing device 105 can prompt the user with the haptic device to provide the input about the event 200.

The computing device 105 can receive a message indicating an event identification request from a second vehicle 101. Based on the event identification request, the computing device 105 can prompt the user to identify the event 200. That is, the second vehicle 101 can collect data 115 indicating an event 200, but may require additional data 115 about the objects 210 to identify the event 200. Thus, the second vehicle 101 can send a message to the first vehicle 101 computing device 105 for additional data 115 about the objects 210. Upon receiving the message from the second vehicle 101, the computing device 105 can prompt the user on the wearable device 140 display to provide input about the objects 210. The computing device 105 can then send a message with the user input to the second vehicle 101. Furthermore, if the computing device 105 can identify the event 200 based on the user input about the objects 210, the computing device 105 can send a message to the second vehicle 101 identifying the event 200.

Figure 3:
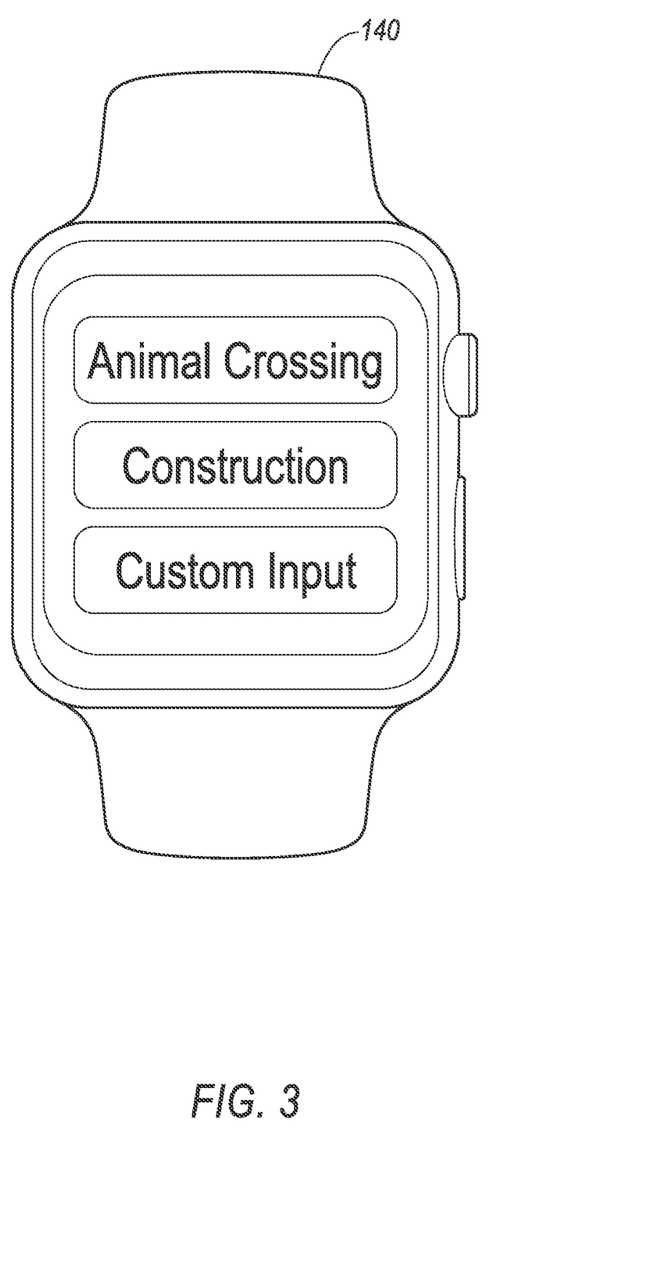
FIG. 3 illustrates an example wearable device including the prompt for user input.

FIG. 3 illustrates an example wearable device 140 prompting the user for input about the event 200. The wearable device processor 145 can display a plurality of prompts on the wearable device 140 display. Upon receiving input, the wearable device processor 145 can send a message to the computing device 105 with the input. The computing device 105 can then identify the event 200 based on the input. In the example of FIG. 3, the wearable device processor 145 displays three prompts: one for an animal crossing event 200, one for a construction event 200, and one for providing custom user input about the event 200. That is, the wearable device processor 145 can display prompts related to stored events (e.g., the animal crossing, the construction, etc.) and prompts to allow the user to provide a custom input. When the objects 210 indicate an event 200 that is not one of the events 200 presented by prompts, the user can provide a custom input to identify the objects 210. For example, the custom input can be an audio input, and the computing device 105 can use known speech-parsing techniques to identify the text of the audio input to identify the objects 210 and the event 200. In another example, the custom input can be a text input from a virtual keyboard displayed on the wearable device 140 display.

Figure 4:
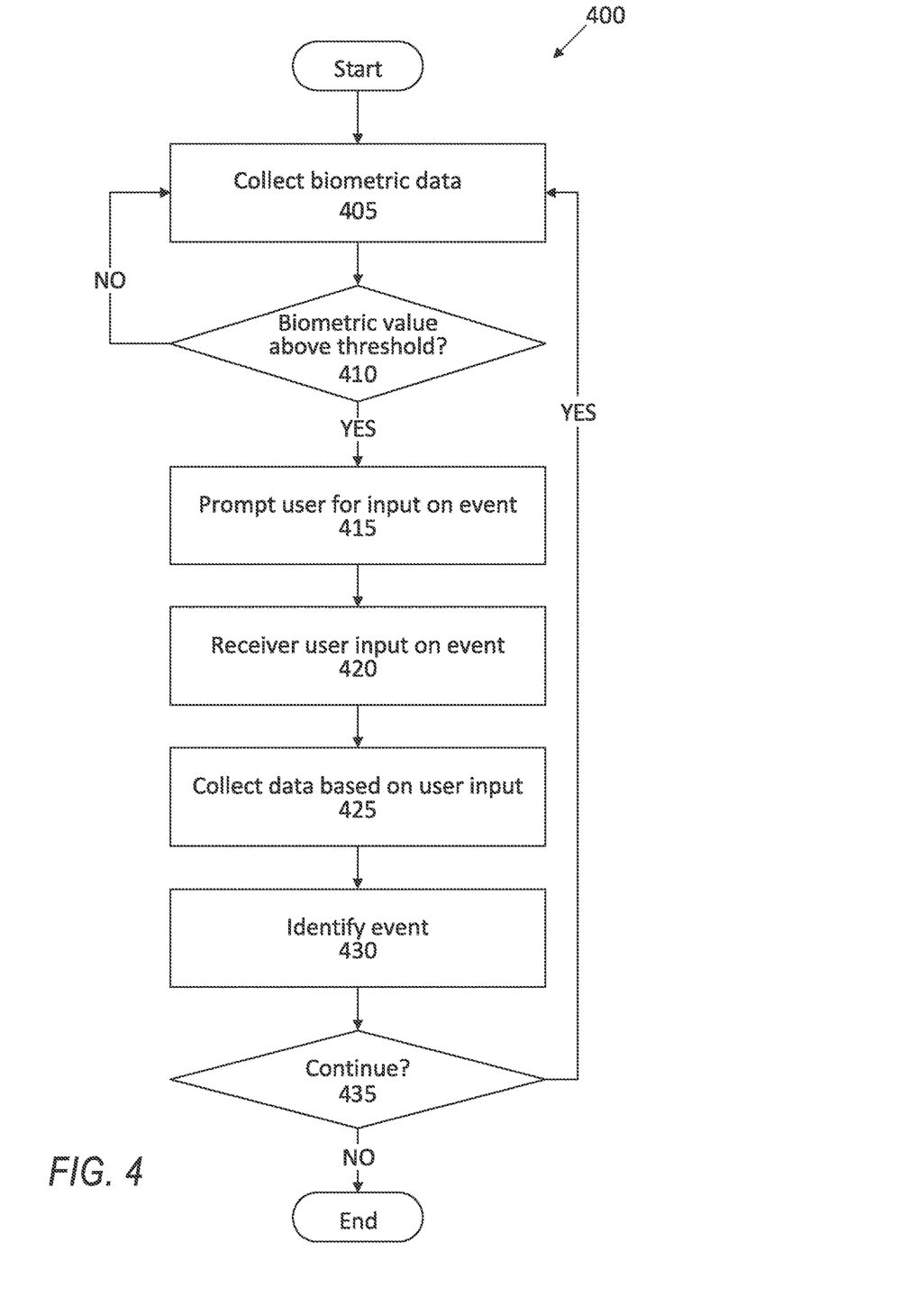
FIG. 4 is a block diagram of an example process for prompting the user to identify the event based on user biometric data.

FIG. 4 illustrates an example process 400 for prompting a user to identify an event 200. The process 400 begins in a block 405 in which the computing device 105 instructs the wearable device processor 145 to actuate one or more sensors 160 in the wearable device 140 to collect biometric data 115 from the user. As described above, for example, the wearable device processor 145 can receive data 115 from sensors 160 of the user's galvanic skin response and/or heart rate.

Next, in a block 410, the wearable device processor 145 determines whether the biometric data 115 exceeds a predetermined threshold. For example, if the biometric data 115 collected are galvanic skin response data 115, the wearable device processor 145 can compare the measured galvanic skin response to a skin response threshold. In another example, if the biometric data 115 collected are heart rate data 115, the wearable device processor 145 can compare the measured heart rate to a heart rate threshold. If the biometric data 115 exceed the predetermined threshold, the process 400 continues in a block 415. Otherwise, the process 400 returns to the block 405 to collect more biometric data 115.

In the block 415, the wearable device processor 145 prompts the user for input on one or more objects 210 near the vehicle 101 in response to biometric data indicating an event 200 as described above regarding the block 410. The wearable device processor 145 can provide the prompts on the wearable device 140 display. As described above, biometric data 115 above the threshold can indicate that the user is sweating and/or is tense from witnessing an event 200. Thus, the wearable device processor 145 can prompt the user to provide input about objects 210 near the vehicle 101 that the computing device 105 may have difficulty identifying based solely on data 115 from vehicle 101 sensors 110.

Next, in a block 420, the wearable device processor 145 receives an input from the user. The input can be, e.g., an audio input recorded by a microphone in the wearable device 140, a text input, an option on a menu on the wearable device 140 display etc. The wearable device processor 145 can send the input to the computing device 105 over the network 125.

Next, in a block 425, the computing device 105 actuates one or more sensors 110 to collect data 115 about the objects 210 based on the input received from the wearable device processor 145. For example, the computing device 105 can use a text-parsing technique to convert an audio input into data 115 that the computing device 105 can examine. Based on the data 115 from the audio input, the computing device 105 can use the sensors 110 to collect data 115 about the objects 210. For example, the computing device 105 can actuate a camera 110 to collect visual data 115 of the objects 210 on the roadway 205 in front of the vehicle 101 based on an audio input indicating that the event 200 is occurring in front of the vehicle 101.

Next, in a block 430, the computing device 105 identifies the event 200 based on the data 115 and the user input. For example, if the data 115 indicate objects 210 moving across the roadway 205 in front of the vehicle 101 and the user input includes the word "deer," the computing device 105 can identify the event 200 as deer crossing the roadway.

Next, in a block 435, the computing device 105 determines whether to continue the process –400. For example, if the vehicle 101 has stopped and powered off, the computing device 105 can determine not to continue the process 400. If the computing device 105 determines to continue, the process 400 returns to the block 405 to collect more biometric data 115. Otherwise, the process 400 ends.

Figure 5:
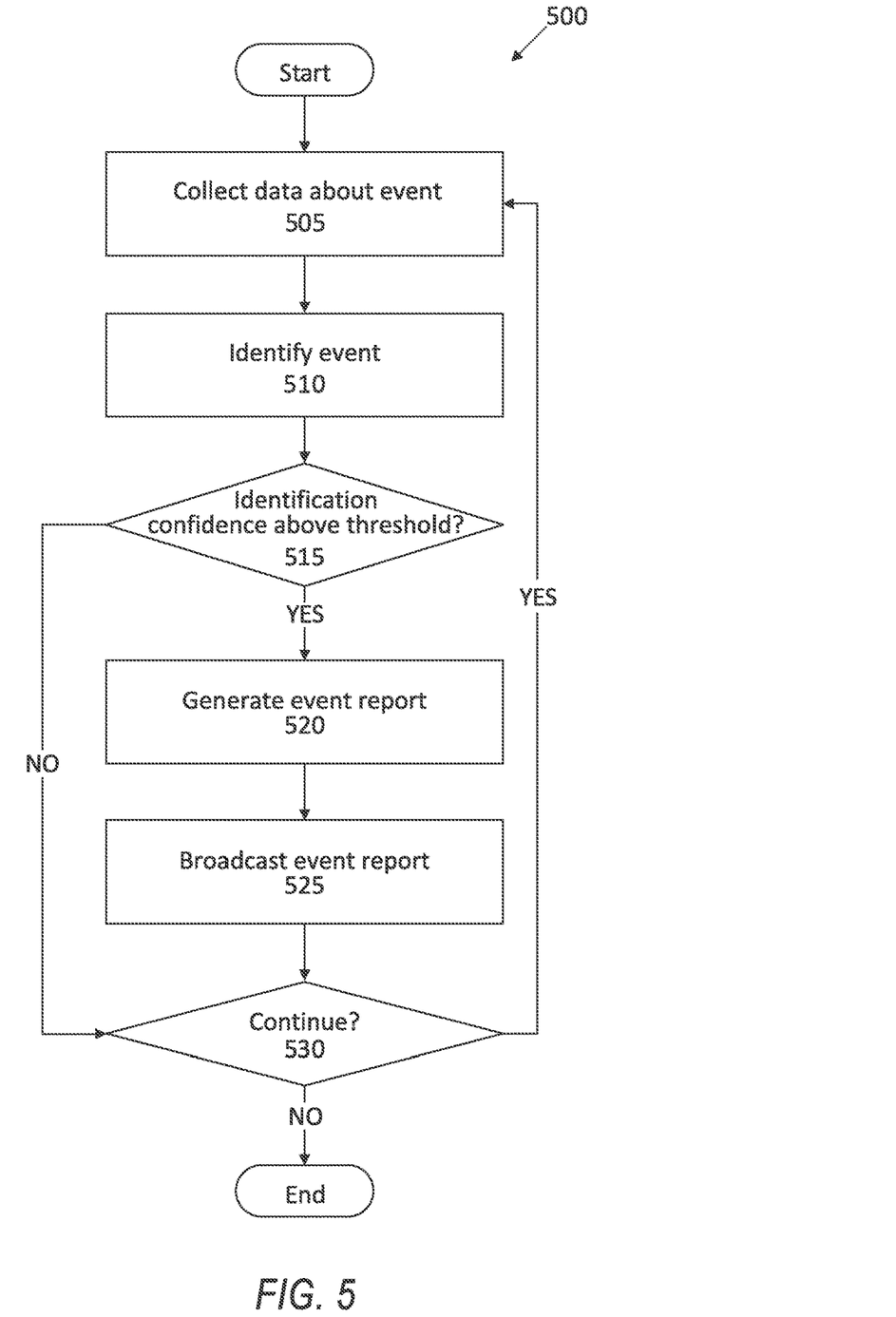
FIG. 5 is a block diagram of an example process for broadcasting an event report based on the identified event.

FIG. 5 illustrates an example process 500 for broadcasting information about events 200. As described above, the computing device 105 can communicate with other vehicles 101 to collect data 115 about objects 210 related to events 200 on the roadway 205. By communicating with other vehicles 101, the events 200 can be identified with greater confidence than if working only from data 115 provided by vehicle 101 sensors 110. The process 500 begins in a block 505, in which the computing device 105 collects data 115 from sensors 110 about one or more objects 210. As described above, upon instruction from the user device processor 155 and/or the wearable device processor 145, the computing device 105 can collect the data 115 about the objects 210.

Next, in a block 510, the computing device 105 identifies the event 200. Based on the user input and the data 115 about the objects 210, the computing device 105 can assign a classification to the event 200, as described above. For example, the computing device 105 can identify the event 200 as, e.g., an animal crossing, an obstacle, a traffic incident, etc.

Next, in a block 515, the computing device 105 assigns an identification confidence value to the event 200 and determines whether the identification confidence value is above a predetermined threshold. As described above, the computing device 105 can use known confidence-determining techniques (e.g., evaluating the quality of the data 115) to determine the identification confidence value. If the identification confidence value for the event 200 is above the threshold, the process 500 continues in a block 520. Otherwise, the process 500 continues in the block 530.

In the block 520, the computing device 105 generates an event report. The event report can be a message that includes the identified event 200 and a current location of the vehicle 101. Thus, the event report can be used by other vehicles 101 to predict the event 200 or a similar event 200 when near the location identified in the event report.

Next, in a block 525, the computing device 105 broadcasts the event report. The computing device 105 can send the event report over the network 125, e.g., WiFi, DSRC, Bluetooth®, etc. The computing device 105 can broadcast the event report to other vehicles 101, the server 130, etc.

In the block 530, the computing device 105 determines whether to continue the process 500. For example, if the computing device 105 determines that the vehicle 101 is not moving and a gear selector is in a parked position, the computing device 105 can determine not to continue the process 500. In another example, if the computing device 105 determines that the vehicle 101 is still travelling along the roadway 205, the computing device 105 can determine to continue the process 500. If the computing device 105 determines to continue, the process 500 returns to the block 505 to collect more data 115. Otherwise, the process 500 ends.

As used herein, the adverb "substantially" modifying an adjective means that a shape, structure, measurement, value, calculation, etc. may deviate from an exact described geometry, distance, measurement, value, calculation, etc., because of imperfections in materials, machining, manufacturing, data collector measurements, computations, processing time, communications time, etc.

Computing devices 105 generally each include instructions executable by one or more computing devices such as those identified above, and for carrying out blocks or steps of processes described above. Computer-executable instructions may be compiled or interpreted from computer programs created using a variety of programming languages and/or technologies, including, without limitation, and either alone or in combination, Java™, C, C++, Visual Basic, Java Script, Perl, HTML, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media. A file in the computing device 105 is generally a collection of data stored on a computer readable medium, such as a storage medium, a random access memory, etc.

A computer-readable medium includes any medium that participates in providing data (e.g., instructions), which may be read by a computer. Such a medium may take many forms, including, but not limited to, non-volatile media, volatile media, etc. Non-volatile media include, for example, optical or magnetic disks and other persistent memory. Volatile media include dynamic random access memory (DRAM), which typically constitutes a main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

With regard to the media, processes, systems, methods, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. For example, in the process 300, one or more of the steps could be omitted, or the steps could be executed in a different order than shown in FIG. 3. In other words, the descriptions of systems and/or processes herein are provided for the purpose of illustrating certain embodiments, and should in no way be construed so as to limit the disclosed subject matter.

Accordingly, it is to be understood that the present disclosure, including the above description and the accompanying figures and below claims, is intended to be illustrative and not restrictive. Many embodiments and applications other than the examples provided would be apparent to those of skill in the art upon reading the above description. The scope of the invention should be determined, not with reference to the above description, but should instead be determined with reference to claims appended hereto and/or included in a non-provisional patent application based hereon, along with the full scope of equivalents to which such claims are entitled. It is anticipated and intended that future developments will occur in the arts discussed herein, and that the disclosed systems and methods will be incorporated into such future embodiments. In sum, it should be understood that the disclosed subject matter is capable of modification and variation.

The article "a" modifying a noun should be understood as meaning one or more unless stated otherwise, or context requires otherwise. The phrase "based on" encompasses being partly or entirely based on.

What is claimed is:

1. A system, comprising a computer including a processor and a memory, the memory storing instructions executable by the processor to:
   collect biometric data about a user in a vehicle with one or more sensors in a wearable device;
   based on the biometric data from the wearable device, prompt a user to provide an input on the wearable device to identify an object exterior to the vehicle on or near a roadway;
   collect data about the object based on the provided input;
   determine a confidence value that an event includes detection of the identified object on or near the roadway based on the collected data; and
   identify an event caused by the identified object that disrupts operation of the vehicle based on the confidence value, the user input, and the identified object.

2. The system of claim 1, wherein the computer is further programmed to actuate a vehicle sensor upon receiving the input.

3. The system of claim 1, wherein the computer is further programmed to prompt the user upon receiving a request from another vehicle to identify the object.

4. The system of claim 1, wherein the computer is further programmed to stop prompting a predetermined period of time after a biometric data threshold had been met and user input has not been received.

5. The system of claim 1, wherein:
   the biometric data include a galvanic skin response of the user; and
   the computer is further programmed to prompt the user when the galvanic skin response exceeds a galvanic skin response threshold.

6. The system of claim 1, wherein:
   the biometric data include a heart rate of the user; and
   the computer is further programmed to prompt the user when the heart rate exceeds a heart rate threshold.

7. The system of claim 1, wherein the computer is further programmed to send a message to another vehicle with the input from the user identifying the object.

8. The system of claim 1, wherein the computer is further programmed to present captured visual data of the object on a display of the wearable device.

9. The system of claim 1, wherein the computer is further programmed to collect data with a vehicle sensor and, based on the data from the vehicle sensor and the biometric data, prompt the user to provide the input on the wearable device to identify the object.

10. The system of claim 1, wherein the computer is further programmed to prompt the user to select one of a plurality of prompts on a display of the wearable device identifying the object.

11. A method, comprising:
    collecting biometric data about a user in a vehicle with one or more sensors in a wearable device;
    based on the biometric data from the wearable device, prompting a user to provide an input on the wearable device to identify an object exterior to the vehicle on or near a roadway;
    collecting data about the object based on the provided input;
    determining a confidence value that an event includes detection of the identified object on or near the roadway based on the collected data; and
    identifying an event caused by the identified object that disrupts operation of the vehicle based on the confidence value, the user input, and the identified object.

12. The method of claim 11, further comprising actuating a vehicle sensor upon receiving the input.

13. The method of claim 11, further comprising prompting the user upon receiving a request from another vehicle to identify the object.

14. The method of claim 11, further comprising stopping to prompt the user after a predetermined period of time after a biometric data threshold had been met and user input has not been received.

15. The method of claim 11, wherein the biometric data include a galvanic skin response, the method further comprising prompting the user when the galvanic skin response exceeds a galvanic skin response threshold.

16. The method of claim 11, wherein the biometric data include a heart rate of the user, the method further comprising prompting the user when the heart rate exceeds a heart rate threshold.

17. The method of claim 11, further comprising sending a message to another vehicle with the input from the user identifying the object.

18. The method of claim 11, further comprising presenting captured visual data of the object on a display of the wearable device.

19. The method of claim 11, further comprising collecting data with a vehicle sensor and, based on the data from the vehicle sensor and the biometric data, prompting the user to provide the input on the wearable device to identify the object.

20. The method of claim 11, further comprising prompting the user to select one of a plurality of prompts on a display of the wearable device identifying the object.

* * * * *